United States Patent [19]

Haupt et al.

[11] 4,309,339

[45] Jan. 5, 1982

[54] LEUCINE-RICH 3,1-S-$\alpha_2$-GLYCOPROTEIN, PROCESS FOR ISOLATING IT AND ITS USE

[75] Inventors: Heinz Haupt; Siegfried Baudner, both of Marburg, Fed. Rep. of Germany

[73] Assignee: Behringwerke Aktiengesellschaft, Marburg, Fed. Rep. of Germany

[21] Appl. No.: 103,868

[22] Filed: Dec. 14, 1979

Related U.S. Application Data

[63] Continuation of Ser. No. 898,437, Apr. 20, 1978, abandoned.

[30] Foreign Application Priority Data

Apr. 25, 1977 [DE] Fed. Rep. of Germany ....... 2718325

[51] Int. Cl.$^3$ ............................................. C07G 7/00
[52] U.S. Cl. ........................... 260/112 B; 260/112 R; 424/85; 424/88; 424/101; 424/12
[58] Field of Search ....................... 260/112 R, 112 B; 424/101, 85, 88

[56] References Cited

U.S. PATENT DOCUMENTS

| | | | |
|---|---|---|---|
| 3,928,580 | 12/1975 | Fontaine | 260/112 B X |
| 4,041,021 | 8/1977 | Bohn | 260/112 B |
| 4,191,533 | 3/1980 | Bohn et al. | 260/112 B |
| 4,217,339 | 8/1980 | Bohn et al. | 424/12 |

OTHER PUBLICATIONS

Centonze et al., Chem. Abstracts, vol. 51=16,804c (1957).
Centonze et al., Chem. Abstracts, vol. 55=23,724f (1961).
Bohn et al., Chem. Abstracts, vol. 76: 70,559g (1972).
Bohn, Chem. Abstracts, vol. 76: 32,096w (1972).
Bohn, Chem. Abstracts, vol. 80, 79,744d (1974).
Haupt et al., Chem. Abstracts, vol. 65=15,861f (1966).
Higashi, Chem. Abstracts, vol. 57=10,481(c) (1962).

*Primary Examiner*—Howard E. Schain
*Attorney, Agent, or Firm*—Curtis, Morris & Safford

[57] ABSTRACT

New glycoprotein having the following properties:
a sedimentation constant in the ultracentrifuge of 3.1 S±0.2; molecular weight 49,600±4,000;
electrophoretic mobility in the range of the $\alpha_2$-globulins of the human serum;
isoelectric range pH 3.8 to 4.1;
extinction coefficient E 1 cm, 280 nm=1% 7.0±0.2;
content of about 77±2% of $\alpha$-amino acids with a proportion of 17±2% of leucine and about 22% of carbohydrates;
specific immunological reaction with antibodies directed against the glycoprotein;

which can be isolated from human sera and which may be used for the preparation of antisera enabling the detection and determination of the glycoprotein in body fluids.

5 Claims, No Drawings

LEUCINE-RICH 3,1-S-$\alpha_2$-GLYCOPROTEIN, PROCESS FOR ISOLATING IT AND ITS USE This is a continuation of application Ser. No. 898,437, filed Apr. 20, 1978, now abandoned.

The invention relates to a new glycoprotein, to its isolation from human sera and its use for the manufacture of antisera which are directed against the said glycoprotein and with the aid of which the content of said glycoprotein in body fluids can be proved and measured.

With regard to its physical and immunochemical properties, the new glycoprotein differs considerably from the hitherto described proteins isolated from human serum.

Now, the object of the present invention is a glycoprotein which is characterized by the following parameters:

(a) sedimentation constant in the ultracentrifuge 3.1 S±0.2

(b) molecular weight 49,600±4,000

(c) electrophoretic mobility in the range of $\alpha_2$-globulins of the human serum (d) iso-electric range pH 3.8 to 4.1

(e) extinction coefficient E 1 cm, 280 nm=1% 7±0.2

(f) content of about 77±2% of $\alpha$-aminoacids with a content of 17±2% of leucine and about 22% of carbohydrates (g) specific immunological reaction to antibodies which are directed against the glycoprotein.

For determining the parameters, the following analytical methods were used:

Ultracentrifugation analysis was carried out with an ultracentrifuge of Messrs. Beckman, Model E. For this ultracentrifugation analysis, the protein was employed in a concentration of 0.2% (g/v) in a 0.9% strength sodium chloride solution. Sedimentation was effected at 60000 rev./min. in a superposing cell. Recording was effected according to the UV-scanner technique at 280 nm. Determination of the therefrom derived molecular weight was effected according to the equilibrium method described by Yphantis.

Isoelectric focusation was effected with the aid of an apparatus marketed by Messrs. LKB, Stockholm, Sweden, and with the reagents sold by said firm. A 440 ml column with special buffer substances was used for this purpose in the pH-range of from 3 to 6.

Analysis for carbohydrates was effected in accordance with the method described by Schultze, Schmidtberger, Haupt (1958), Biochem. Z., Volume 329, pages 490-507.

Analysis for amino-acids was carried out in accordance with the method described by Spackman, Stein and Moore (1958), Anal. Chem. 30, page 1190. An amino-acid analyzer Multichrome B of Messrs. Beckman was used.

The immunological test of the new glycoprotein was effected using an antiserum obtained by immunizing rabbits during a period of time of 6 weeks with the isolated protein with complete Freund's adjuvant. The quantitative determination of the protein with the aid of this serum can be carried out according to the method described by Laurell (1966), Analyt. Biochem., Volume 15, pages 45-52.

In view of the striking parameters of the new protein, i.e. the relatively low sedimentation constant of 3.1S±0.2, the outstanding high content of leucine and the easy identificability by the migration up to pH 8.6 in the $\alpha_2$-range of proteins, the new protein has been designated as the leucine-rich 3.1-S-$\alpha_2$-glycoprotein.

The present invention furthermore relates to a process for the isolation of the leucine-rich 3.1S-$\alpha_2$-glycoprotein. Starting from solutions which contain this protein, in particular human blood serum, the protein is enriched by several process steps until it is pure. The aim of these enrichment steps is either to obtain the protein as free as possible from other serum components or to precipitate accompanying serum components and to retain the 3.1 S-$\alpha_2$-glycoprotein in solution.

Accordingly, the object of the invention is a process for isolating the leucine-rich 3.1-S-$\alpha_2$-glycoprotein, in which at least one of the following process steps is used until obtention of the pure product:

(a) Addition of a neutral salt usually employed for the fractionation in protein chemistry until the leucine-rich 3.1-S-$\alpha_2$-glycoprotein is precipitated, preferably ammonium sulfate in a quantity of from 2.4 to 2.8 M/l, at a neutral pH-value;

(b) Addition of an organic solvent usually employed for the fractionation in protein chemistry up to a concentration at which the leucine-rich 3.1-S-$\alpha_2$-glycoprotein still remains in solution and accompanying proteins are precipitated, preferably by the addition of 40% (v/v) of ethanol to a solution buffered in a weakly acid pH-range at a temperature of $-8°$ to $0°$ C., preferably $-5°$ C.

This precipitation behaviour of the glycoprotein means that it remains in solution when subjected to the known plasma fractionation processes with the aid of ethanol according to the method VI described by Cohn (E. J. Cohn et al., J. Am. Chem. Soc. 68 (1946), page 459). The alcoholic supernatant remaining in this precipitation process contains only 1-26 plasma proteins at all. To an expert this means that the fractionation process according to Cohn is particularly suited for enriching the new glycoprotein over other plasma proteins.

(c) Addition of water-soluble salts of acridine bases, preferably 2-ethoxy-6,9-diaminoacridine lactate, up to a concentration of 0.01 Mole/l in the neutral to weakly alkaline pH range. In this process, the new 3.1-S-$\alpha_2$-glycoprotein is not precipitated, whereas the major part of plasma proteins, with exception of the gammaglobulins, is precipitated.

Accordingly, a fractionated precipitation of a protein solution which still contains other plasma proteins in addition to the leucine-rich 3.1-S-$\alpha_2$-glycoprotein with the aid of acridine bases is an advantageous method for purifying the new glycoprotein, because a large part of the accompanying proteins is separated by precipitation.

(d) Addition of such organic acids which are usually employed in protein chemistry for precipitating proteins, preferably trichloroacetic acid, up to a concentration of 0.2 Mole/l, while the leucine-rich 3.1-S-$\alpha_2$-glycoprotein remains in solution.

It is known that this method enables the precipitation of the globulin fraction of the plasma proteins. Thus, this method too, is suitable for enriching the new glycoprotein in solution.

Instead of trichloroacetic acid, other acids may likewise be used for enriching the new glycoprotein, for example perchloric acid or sulfosalicyclic acid. With perchloric acid, the final concentration usually employed for the fractionation is in the range of from 0.4 to 0.6 Mole/l. At those concentration the new glycoprotein remains in solution.

(e) Heating for a short time to a temperature of almost 100° C. at a neutral to weakly acidic pH-value the protein solution containing the leucine-rich 3.1-S-$\alpha_2$-glycoprotein. The so-called "heat-coagulation" of protein solutions is preferably effected at a pH-value of about 5 for a period of time of 5 to 15 minutes at 95°-98° C. It has been found that, after one process step, the 3.1-S-$\alpha_2$-glycoprotein remains in solution. Under equal conditions only a few proteins remain in solution. Most of them precipitate from the solutions while coagulating.

(f) Removal of electrolytes from the solution containing the leucine-rich 3.1-S-$\alpha_2$ glycoprotein. Reduction of the content of electrolytes of a protein solution leads to the precipitation of the so-called euglobulins. These encompass a part of the lipoproteins, the macroglobulins, a part of the immunoglobulins and ceruloplasmine, cited by way of example. In this method, designated as euglobulin precipitation, the leucine-rich-3.1 S-$\alpha_2$-glycoprotein remains in solution.

The reduction of the electrolyte content of a solution can be effected according to several methods, for example with the aid of dialysis against an aqueous medium with reduced conductivity, optionally against distilled water. Electrodialysis processes or the reduction of the electrolytes in solution with the use of ion exchangers are likewise suitable for this purpose.

(g) Molecular sieve fractionation of the solution containing the new glycoprotein with the aim of enriching proteins with a molecular weight of between 45,000 and 55,000 and exclusion of proteins having a higher or lower molecular weight. For this purpose, column fractionation is suitably used using molecular sieving gels, preferably dextran cross-linked with epichlorhydrine. But other gel filtration media with comparable exclusion or fractionation limits are likewise suitable.

(h) Treatment of the protein solution containing the leucine-rich 3.1-S-$\alpha_2$-glycoprotein with an anion exchanger, preferably such an anion exchanger which contains aminoethyl, diethylaminoethyl or triethylaminoethyl as functional groups and cellulose as matrix. The leucine-rich 3.1-S-$\alpha_2$-glycoprotein is bound to such an ion exchanger from a solution having an ion strength of 2=0.05. Thus, it can be separated thereafter with the ion exchanger from the other proteins which remain in solution. The new protein can be eluted by increasing the conductivity with the aid of, for example neutral salts such as sodium chloride, and therewith enriched over other accompanying proteins.

(e) Electrophoresis in suitable carrier media and isolation of the zone of the $\alpha_2$-range of the plasma proteins.

(k) Treatment of the solution containing the leucine-rich 3.1-S-$\alpha_2$-glycoprotein with water-insoluble calcium phosphate hydrate, preferably hydroxyl apatite. The new glycoprotein is not absorbed on to the insoluble phosphate even not at a low ion strength of the protein solution, for example 1/1000 moles/l of ions. In case of previously purified protein solution containing the new protein, the supernatant or, in column chromatography, the eluate represents the solution of the purified 3.1-S-$\alpha_2$-glycoprotein.

As last of afore-mentioned process steps, the eluate of the column yields the pure glycoprotein.

The new leucine-rich 3.1-S-$\alpha_2$-glycoprotein can be enriched to any desired degree and prepared in pure form by any combination of the process steps which are usual in protein chemistry, from protein solutions which contain said protein, for example human serum or a fraction thereof. The solution obtained finally which contains only the leucine-rich 3.1-S-$\alpha_2$-glycoprotein and optionally salts can be freed from electrolytes and lyophilized.

A preferred process for the isolation of the leucine-rich 3.1-S-$\alpha_2$-glycoprotein starts from the known serum fractionation with the aid of 2-ethoxy-6,9-diaminoacridine lactate and ammonium sulfate, generally known under the designation "Rivanol-ammonium sulfate process" described by Schultze, Hermanns, Molecular Biology of Human Proteins, Elsevier Publishing Company (1966), page 265. In this process, the leucine-rich 3.1-S-$\alpha_2$-glycoprotein together with a number of other glycoproteins is enriched in a solution obtained as side fraction in the isolation of albumin and gammaglobulin from human serum. From this solution, a number of accompanying proteins is precipitated in a first separation step with the aid of 2-ethoxy-6,9-diaminoacridine lactate in a concentration of 0.03 to 0.06 m/l. The precipitating agent is precipitated by the addition of chloride ions, preferably sodium chloride. The protein solution is combined with an ion exchanger which is capable of binding the leucine-rich-S-$\alpha_2$-glycoprotein. For this purpose, an anion exchanger with functional aminoethyl-, diethylaminoethyl- or triethylaminoethyl groups is advantageously used.

The ion exchanger is then treated with a buffer solution with rising salt concentration. By this measure, the new protein is again separated from the ion exchanger. The solution is then subjected to a molecular sieving process in which proteins having a molecular weight of 100,000-150,000 are separated. The low molecular fraction contains the leucine-rich 3.1-S-$\alpha_2$-glycoprotein besides other, low-molecular glycoproteins.

It is suitable and advantageous to repeat the ion exchange chromatography under somewhat varying conditions. This can be done, on the one hand, by varying the adsorption or elution conditions or, on the other hand, by selecting ion exchangers with different basicity. The glycoprotein is freed from remaining impurities by a treatment with a mineral adsorbant, for example hydroxylapatite. Thereby the accompanying proteins remain bound to the adsorbant whereupon a solution with pure leucine-rich 3.1-S-$\alpha_2$-glycoprotein is obtained.

The leucine-rich 3.1-S-$\alpha_2$-glycoprotein is immunogenic. Its parenteral administration to vertebrate animals, preferably to the usual laboratory animals such as rabbits, leads to the formation of antibodies in the blood of these animals. This blood can then be withdrawn and the serum is separated or enriched with regard to existing antibodies. For this purpose the expert may use the habitual methods of the plasma protein fractionation. By immunizing the test animals with the isolated 3.1-S-$\alpha_2$-glycoprotein, an antiserum was obtained which reacts strongly specifically with the immunization antigen. Cross-reactions with other hitherto isolated serum proteins were not observed.

Thus, the new leucine-rich 3.1-S-$\alpha_2$-glycoprotein is a valuable immunizing agent in the preparation of antisera. The latter are valuable diagnostic reagents.

Accordingly, the object of the invention is the use of the new glycoprotein for the preparation of antisera.

The quantitative immunological determinations of the protein with the aid of the electro-immuno assay according to Laurell in a mixture of sera of about 1000 donors showed an average content of 3.1-S-$\alpha_2$-glycoprotein of 2.1 mg/100 ml of serum.

It was found that the concentration of the leucine-rich 3.1-S-$\alpha_2$-glycoprotein in the individual sera of adults varies between 1.5 and 3.2 mg/100 ml of serum.

The invention is illustrated by the following Example.

EXAMPLE

The starting material for the isolation of the leucine-rich 3.1-S-$\alpha_2$-glycoprotein is a fraction obtained from 25 liters of human plasma. This is treated with 0.84% of 2-ethoxy-6,9-diaminoacridine lactate at pH 8.0. The precipitating agent is precipitated from the supernatant as chloride and removed, then precipitation is effected at pH 7.0 with 2.0 moles of ammonium sulfate. This precipitate as gammaglobulin-rich fraction is separated and the supernatant is subjected to the following process.

The supernatant is concentrated to 5 l by ultrafiltration. The protein content of the solution is then 3%. The solution is washed with a 0.85% strength sodium chloride solution at the ultrafilter and then combined with 7.5 g of 2-ethoxy-6,9-diaminoacridine lactate. The precipitate formed is separated by centrifugation. Sodium chloride is added to the supernatant solution until a final concentration of 5% (g/v). Thereupon the acridine base precipitates as chloride. It is separated by centrifugation. The supernatant is freed from sodium chloride by washing on the ultrafilter and equilibrated with 0.02 m of phosphate buffer, pH 7.0. It represents 3 liters of a 2.5% strength protein solution. 300 g of diethylaminoethyl-cellulose ion exchanger are added, the whole is stirred for 1 hour, suction-filtered and the filter residue is washed with 0.02 M/l of phosphate buffer, pH 7.0. The ion exchanger is then washed with a 1 M NaCl solution. The through flow is partly removed. One fraction which contains the leucine-rich glycoprotein is further processed. This fraction is subjected to gel-filtration on SEPHADEX G 150; the gel-filtration is effected in a column having a diameter of 20 cm and a height of 1 m and which is filled with SEPHADEX$^{(R)}$ G 150. The eluant is trishydroxymethylaminoethane-HCl buffer, 0.1 molar, having a pH-value of 8.0 and containing 1 Mole of NaCl. Thereby, a high-molecular fraction is separated and a low-molecular fraction is obtained which contains the 3.1-S-$\alpha_2$-glycoprotein.

Then, a column (about 500 ml, 5×45 cm) is filled with diethylaminoethyl-SEPHADEX ion exchanger, the fraction containing the leucine-rich-3.1-S-$\alpha_2$-glycoprotein is introduced into the column and elution of the substances is effected with a linear salt gradient of 0.006 M of trishydroxymethylaminomethane-HCl buffer having a pH-value of 8.6 without addition of salt to 0.006 M of trishydroxymethylaminomethane buffer HCl having a pH-value of 8.6 and containing 0.2 M/l NaCl. The eluate is collected in fractions. Those fractions are further processed which show an electric mobility in the $\alpha_2$-range of the proteins by a control electrophoresis. For enriching the protein, the fractions are combined with ammonium sulfate until a saturation of 70% is reached. The precipitate formed is isolated by centrifugation, dissolved in water and dialyzed against the same buffer as that used for the following QAE-chromatography.

Then, a further chromatography on QAE-SEPHADEX is effected in a comparable test arrangement. For the elution, a linear salt gradient of 0.08 mole of sodium acetate buffer, pH 5.5, to 0.35 mole sodium acetate buffer pH 5.5 is used. The fractions characterized by electrophoresis are isolated and further processed.

At first, dialysis against 0.001 mole of sodium phosphate buffer having a pH-value of 7.0 is carried out. The product equilibrated against this buffer is introduced into a column filled with hydroxylapatite (size of the column 4×12 cm). The contents of the column is eluted with 0.001 mole of phosphate buffer pH 7.0. The eluate represents pure leucine-rich 3.1-S-$\alpha_2$-glycoprotein.

Starting from 25 liters of human plasma, 100 mg of the protein of the invention are obtained.

It has the following composition of aminoacids:

| Amino-acids | Mole % of the amino-acid proportion | Variation coefficient % |
|---|---|---|
| Lysine | 3.87 | 5.90 |
| Hystidine | 2.23 | 11.28 |
| Arginine | 4.65 | 7.68 |
| Aspartic acid | 11.45 | 1.49 |
| Threonine | 3.87 | 6.26 |
| Serine | 6.43 | 2.36 |
| Glutamic acid | 10.72 | 2.51 |
| Proline | 7.04 | 4.43 |
| Glycine | 7.32 | 2.31 |
| Alanine | 6.65 | 1.97 |
| ½ Cystine | 1.21 | 9.83 |
| Valine | 4.48 | 3.78 |
| Methionine | 0.75 | 5.81 |
| Isoleucine | 1.29 | 3.16 |
| Leucine | 22.05 | 5.79 |
| Tyrosine | 0.81 | 19.53 |
| Phenylalanine | 3.23 | 1.39 |
| Tryptophane | 1.60 | 11.69 |

| Carbohydrate | % by weight |
|---|---|
| Galactose | 4.1 ± 0.3 |
| Mannose | 3.8 ± 0.3 |
| Glucose | 0 |
| Fucose | 0.3 ± 0.1 |
| Xylose | 0 |
| N-Acetylhexosamine | 8.1 ± 0.5 |
| N-Acetylneuraminic acid | 6.6 ± 0.4 |
| Sum (carbohydrate proportion) | 22.9 ± 1.6 |

The variation values indicated represent limit values within the error range, which are inherent in the test method used.

We claim:

1. Glycoprotein isolated from human serum, characterized by the following parameters:
   (a) sedimentation constant in the ultracentrifuge 3.1 S±0.2;
   (b) molecular weight of 49,000±4,000;
   (c) electrophoretic mobility in the range of the $\alpha_2$-globulins of the human serum;
   (d) isoelectric range pH 3.8–4.1;
   (e) extinction coefficient $E_{1\ cm}^{1\%}$, 280 nm=7.0±0.2;
   (f) content of about 77%±2% of $\alpha$-amino-acids and about 23%±2% of carbohydrates, and of said amino acids and carbohydrates, the major fractions being present as follows:

| Amino Acids | Mole % of the amino-acid proportion | Variation coefficient % |
|---|---|---|
| Aspartic acid | 11.45 | 1.49 |
| Serine | 6.43 | 2.36 |
| Glutamic acid | 10.72 | 2.51 |
| Proline | 7.04 | 4.43 |

-continued

| | | |
|---|---|---|
| Glycine | 7.32 | 2.31 |
| Alanine | 6.65 | 1.97 |
| Leucine | 22.05 | 5.79 |

| Carbohydrate Residues | % by weight |
|---|---|
| Galactose | 4.1 ± 0.3 |
| Mannose | 3.8 ± 0.3 |
| N-Acetylhexosamine | 8.1 ± 0.5 |
| N-Acetylneuraminic acid | 6.6 ± 0.4 |

(g) specific immunological reactions with antibodies directed against the glycoprotein.

2. Glycoprotein isolated from human serum, characterized by the following parameters:
 (a) sedimentation constant in the ultracentrifuge 3.1 S±0.2;
 (b) molecular weight of 49,000±4,000;
 (c) electrophoretic mobility in the range of the $\alpha_2$-globulins of the human serum;
 (d) isoelectric range pH 3.8–4.1;
 (e) extinction coefficient $E_1$ $_{cm}^{1\%}$, 280 nm = 7.0±0.2;
 (f) content of about 77%±2% of α-amino-acids and about 23%±2% of carbohydrates, said amino acids and carbohydrates being present as follows:

| Amino Acids | Mole % of the amino-acid proportion | Variation coefficient % |
|---|---|---|
| Lysine | 3.87 | 5.90 |
| Hystidine | 2.23 | 11.28 |
| Arginine | 4.65 | 7.68 |
| Aspartic acid | 11.45 | 1.49 |
| Threonine | 3.87 | 6.26 |
| Serine | 6.43 | 2.36 |
| Glutamic acid | 10.72 | 2.51 |
| Proline | 7.04 | 4.43 |
| Glycine | 7.32 | 2.31 |
| Alanine | 6.65 | 1.97 |
| ½ Cystine | 1.21 | 9.83 |
| Valine | 4.48 | 3.78 |
| Methionine | 0.75 | 5.81 |
| Isoleucine | 1.29 | 3.16 |
| Leucine | 22.05 | 5.79 |
| Tyrosine | 0.81 | 19.53 |
| Phenylalanine | 3.23 | 1.39 |
| Tryptophane | 1.60 | 11.69 |

| Carbohydrate Residues | % by weight |
|---|---|
| Galactose | 4.1 ± 0.3 |
| Mannose | 3.8 ± 0.3 |
| Glucose | 0 |
| Fucose | 0.3 ± 0.1 |
| Xylose | 0 |
| N-Acetylhexosamine | 8.1 ± 0.5 |
| N-Acetylneuraminic acid | 6.6 ± 0.4 |

(g) specific immunological reactions with antibodies directed against the glycoprotein.

3. Process for the isolation of the protein claimed in claim 1, wherein a solution containing said protein is subjected to a combination of the following steps to obtain it in pure form, as demonstrated immunologically whereafter, in each step, the fraction containing said protein is isolated, and the end product recovered after the last step:
 (a) addition of a water-soluble salt of an acridine base up to a concentration of 0.01 moles per liter at a neutral or weakly alkaline pH to precipitate accompanying proteins;
 (b) addition of a neutral salt until the protein precipitates;
 (c) adsorption of the protein on an anion exchanger and elution from it;
 (d) molecular sieve fractionation and isolation of proteins having a molecular weight of between 45,000 and 55,000; and
 (e) adsorption of accompanying proteins with water-insoluble calcium phosphate-hydrate.

4. Process for the isolation of the protein claimed in claim 1, wherein a solution containing said protein is subjected to a combination of the following steps to obtain it in pure form, as demonstrated immunologically whereafter, in each step, the fraction containing said protein is isolated, and the end product recovered after the last step:
 (a) addition of a neutral salt until the protein precipitates;
 (b) addition of an organic solvent until accompanying proteins are precipitated;
 (c) addition of a water-soluble salt of an acridine base until precipitation of accompanying proteins;
 (d) addition of an organic acid until precipitation of accompanying proteins;
 (e) heating to a temperature of between 95° to 100° C. until precipitation of accompanying proteins;
 (f) reduction of the electrolyte content until precipitation of accompanying proteins;
 (g) molecular sieve fractionation and isolation of the proteins having a molecular weight of between 45,000 and 55,000;
 (h) adsorption of the protein on an anion exchanger and elution from it;
 (i) electrophoresis and isolation of the $\alpha_2$-zone of human serum; and
 (k) adsorption of accompanying proteins with water-insoluble calcium phosphate-hydrate.

5. Glycoprotein isolated from human serum, prepared according to the process of claim 4 and further characterized by the following parameters:
 (a) sedimentation constant in the ultracentrifuge 3.1 S±0.2;
 (b) molecular weight of 49,000±4,000;
 (c) electrophoretic mobility in the range of the $\alpha_2$-globulins of the human serum;
 (d) isoelectric range pH 3.8–4.1;
 (e) extinction coefficient $E_1$ $_{cm}^{1\%}$, 280 nm = 7.0±0.2;
 (f) content of about 77%±2% of a α-amino-acids and about 23%±2% of carbohydrates, and of said amino acids and carbohydrates, the major fractions being present as follows:

| Amino Acids | Mole % of the amino-acid proportion | Variation coefficient % |
|---|---|---|
| Aspartic acid | 11.45 | 1.49 |
| Serine | 6.43 | 2.36 |
| Glutamic acid | 10.72 | 2.51 |
| Proline | 7.04 | 4.43 |
| Glycine | 7.32 | 2.31 |
| Alanine | 6.65 | 1.97 |
| Leucine | 22.05 | 5.79 |

| Carbohydrate Residues | % by weight |
|---|---|
| Galactose | 4.1 ± 0.3 |
| Mannose | 3.8 ± 0.3 |
| N-Acetylhexosamine | 8.1 ± 0.5 |
| N-Acetylneuraminic acid | 6.6 ± 0.4 |

(g) specific immunological reactions with antibodies directed against the glycoprotein, which demonstrates the presence of said isolated glycoprotein.

* * * * *